United States Patent [19]

Tone et al.

[11] Patent Number: 5,177,167

[45] Date of Patent: Jan. 5, 1993

[54] OXYGEN-PERMEABLE SHAPED ARTICLES AND PROCESS FOR PRODUCING SAME

[75] Inventors: Seiji Tone, Ohtake; Hiroshi Mori; Naoki Yamamoto, both of Hiroshima; Haruko Takeda, Fujisawa; Masahiro Sugimori, Nagoya, all of Japan

[73] Assignee: Mitsubishi Rayon Co., Ltd., Tokyo, Japan

[21] Appl. No.: 465,180

[22] PCT Filed: Jul. 7, 1989

[86] PCT No.: PCT/JP89/00686

§ 371 Date: Feb. 22, 1990

§ 102(e) Date: Feb. 22, 1990

[87] PCT Pub. No.: WO90/00411

PCT Pub. Date: Jan. 25, 1990

[30] Foreign Application Priority Data

Jul. 8, 1988 [JP] Japan .................... 63-170147
May 11, 1989 [JP] Japan .................... 1-118454

[51] Int. Cl.⁵ .................... C08F 230/08; G02C 7/04
[52] U.S. Cl. .................... 526/279; 351/160 R; 525/278; 264/1.1; 264/2.7; 428/364
[58] Field of Search .................... 526/279; 525/278

[56] References Cited

U.S. PATENT DOCUMENTS

| | | | |
|---|---|---|---|
| Re. 31,406 | 10/1983 | Gaylord | 526/279 |
| 4,235,985 | 11/1980 | Tanaka et al. | 526/279 |
| 4,242,483 | 12/1980 | Novicky | 526/279 |
| 4,424,328 | 1/1984 | Ellis | 526/279 |
| 4,540,761 | 9/1985 | Kawamura et al. | 526/279 |
| 4,625,007 | 11/1986 | Ellis et al. | 526/279 |
| 4,649,185 | 3/1987 | Takamizawa et al. | 526/279 |
| 4,743,667 | 5/1988 | Mizutani et al. | 526/245 |
| 4,861,840 | 8/1989 | Lim et al. | 526/279 |
| 5,023,305 | 6/1991 | Onozuka et al. | 526/279 |
| 5,057,578 | 10/1991 | Spinelli | 526/279 |

FOREIGN PATENT DOCUMENTS

| | | | |
|---|---|---|---|
| 0111663 | 6/1984 | European Pat. Off. | |
| 351859 | 1/1990 | European Pat. Off. | 526/279 |
| 61-264319 | 11/1986 | Japan | 526/279 |
| 62-270912 | 11/1987 | Japan | |
| 63-68668 | 3/1988 | Japan | |
| 1-004640 | 1/1989 | Japan | 526/279 |
| 1-006013 | 1/1989 | Japan | 526/279 |
| 3-012415 | 1/1991 | Japan | 526/279 |
| 3-012416 | 1/1991 | Japan | 526/279 |
| 1338810 | 11/1973 | United Kingdom | |

OTHER PUBLICATIONS

Patent Abstracts of Japan, vol. 13, No. 174 (C-589) (3522), Apr. 25, 1989, & JP-A-1 4640, Jan. 9, 1989, S. Tone, et al., "Block Copolymer Resin Composition".

Patent Abstracts of Japan, vol. 13, No. 174, (C-589) (3522) Apr. 25, 1989, & JP-A-1 4610, Jan. 9, 1989, M. Sugimori, et al., "Preparation of Block Copolymer".

WPIL/Derwent, accession No. 89-050148(07), Derwent Publications Ltd., & JP-A-1 006 013, Jan. 10, 1989.

Database WPIL, accession No. 86-066034 (10), Derwent Publications Ltd., & JP-A-61 018 402, Jan. 27, 1986.

Primary Examiner—Patrick J. Ryan
Assistant Examiner—Jill M. Gray
Attorney, Agent, or Firm—Oblon, Spivak, McClelland, Maier & Neustadt

[57] ABSTRACT

The present invention provides shaped articles having good transparency and high oxygen permeability in a specific direction thereof, which have been made from a block copolymer (a) composed of a polyalkyl methacrylate segment and a silicone-based polymethacrylate segment, or a block copolymer (b) or graft copolymer (c) containing a polyorganosiloxane as one component, according to a process permitting the creation of a specific higher-order structure. These shaped articles have high oxygen permeability at relatively low silicone contents and, therefore, can provide oxygen-permeable products having high tear strength and surface hardness.

9 Claims, No Drawings

OXYGEN-PERMEABLE SHAPED ARTICLES AND PROCESS FOR PRODUCING SAME

DESCRIPTION

1. This invention relates to shaped articles having good transparency and high oxygen permeability, and to a process for producing the same.

2. Background Art

In recent years, contact lenses have been widely popularized as a means for correcting vision defects. This has created a demand for transparent materials having high oxygen permeability, because contact lenses having low oxygen permeability may cause anoxic damage to the cornea.

In response to the demand, shaped articles made from a random copolymer composed chiefly of siloxanyl methacrylate and methyl methacrylate are being used for hard contact lenses.

In order to impart sufficient oxygen permeability to this random copolymer, it is necessary to enhance the content of the silicone-containing component considerably. However, this unavoidably makes it difficult to shape the random copolymer into films, lenses and similar products. Moreover, the resulting shaped articles are not suited for practical purposes because of their relatively low tear strength and surface hardness. In practice, therefore, the content of the silicone-containing component is reduced in consideration of shapability and this makes it impossible to obtain shaped articles having sufficient oxygen permeability.

DISCLOSURE OF THE INVENTION

It is an object of the present invention to provide an oxygen-permeable shaped article which has sufficiently high oxygen permeability for use as an oxygen-permeable membrane, in at least one direction thereof, which has a high degree of transparency permitting it to be formed into contact lenses, and which also has excellent mechanical strength.

According to a first aspect of the present invention, there is provided an oxygen-permeable shaped article consisting of a block copolymer (a) of the general formula A—B, A—B—A or B—A—B where 80% by weight or more of the monomer units constituting segment A comprise an alkyl methacrylate having an alkyl group of 1 to 4 carbon atoms, 80% by weight or more of the monomer units constituting segment B comprise monomer units of the general formula $$CH_2=C(CH_3)COOC_mH_{2m}SiX_3 \quad (1)$$

where m is a whole number of 2 to 5 and each X independently represented a methyl group or

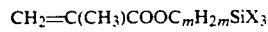

in which n is a whole number of 0 to 30, and the volume fraction of segment B is in the range of 30 to 70%, said shaped article being characterized in that (1) segment A and segment B form microdomains smaller than the wavelengths of visible light, and
(2) the oxygen permeability coefficient thereof is equal to $(0.5 \sim 1) \times (V_A \cdot P_A + V_B \cdot P_B)$ where $V_A$ and $P_A$ represent the volume fraction and oxygen permeability coefficient, respectively, of the segment A component, and $V_B$ and $P_B$ represent the volume fraction and oxygen permeability coefficient, respectively, of the segment B component.

According to a second aspect of the present invention, there is provided an oxygen-permeable shaped article obtained by forming fibers consisting chiefly of a block copolymer (b) or graft copolymer (c) containing an organopolysiloxane as one component, and fusing or bonding a bundle of said fibers to unite them together.

BEST MODE FOR CARRYING OUT THE INVENTION

The first aspect of the present invention will be specifically described hereinbelow.

In the block copolymer (a) used in the first aspect of the present invention, 80% by weight or more, preferably 90% by weight or more, of the monomer units constituting segment A comprise an alkyl methacrylate having an alkyl group of 1 to 4 carbon atoms. Among the alkyl methacrylates having an alkyl group of 1 to 4 carbon atoms, methylmethacrylate is preferred.

The monomers which are copolymerizable with the aforesaid alkyl methacrylates and can constitute segment A include 2,2,2-trichloroethylmethacrylate, glycidyl methacrylate, allyl methacrylate, ethylene dimethacrylate and the like. The number average molecular weight of segment A is preferably in the range of 5,000 to 100,000. If the number average molecular weight is less than 5,000, the resulting shaped article may not have sufficient strength, while if it is greater than 100,000, the resulting shaped article will tend to show a reduction in transparency.

Segment B is such that 80% by weight or more of the monomer units constituting it comprise a silicone-based methacrylate within the scope of the above general formula (1). Preferred examples of such silicone-based methacrylates include tris(trimethylsiloxy)silylpropyl methacrylate, methylbis(trimethylsiloxy)silylpropyl methacrylate, trimethylsilylpropylmethacrylate and compounds of the formula

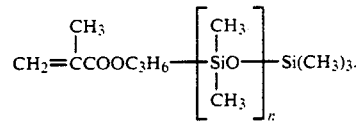

The monomers which are copolymerizable with the aforesaid silicone-based methacrylates and can constitute segment B include dimethylaminoethyl methacrylate, 2-trimethylsiloxyethyl methacrylate, allyl methacrylate, 1H,1H,2H,2H-heptadecafluorodecyl methacrylate and the like. The number average molecular weight of segment B is preferably in the range of 5,000 to 100,000. If the number average molecular weight is less than 5,000, the resulting shaped article will not have sufficient oxygen permeability, while if it is greater than 100,000, the resulting shaped article will show a reduction in transparency and tear strength.

Preferably, the number average molecular weight of the block copolymer (a) as a whole is in the range of 10,000 to 200,000 when the block copolymer (a) is of the A—B type, and in the range of 15,000 to 300,000 when it is of the A—B—A or B—A—B type.

The volume fraction of segment B in the block copolymer (a) should be in the range of 30 to 70%. If the volume fraction of segment B is greater than 70%, the resulting shaped article will have unduly low surface hardness and tear strength, while if it is less than 30%, the resulting shaped article will have insufficient oxygen permeability.

The block copolymers (a) useful in the present invention can be prepared according to any of various well-known ionic polymerization processes. However, it is preferable to employ a radical transfer polymerization process as disclosed in Japanese Patent Laid-Open No. 13603/'83, because this process can control the polymerization degree and composition of each segment with comparative ease.

In the shaped article of the present invention, segments A and B constituting the block copolymer (a) need to form microdomains smaller than the wavelengths of visible light so that the shaped article is transparent. The oxygen permeability of a shaped article made from the block copolymer (a) varies according to the arrangement of the aforesaid microdomains. More specifically, when the microdomains of one segment are interconnected in the desired direction of oxygen passage, the resulting shaped article provides a so-called parallel model. The oxygen permeability coefficient P of this shaped article is given by $P = (V_A \cdot P_A + V_B \cdot P_B)$ where $V_A$ and $P_A$ represent the volume fraction and oxygen permeability coefficient, respectively, of the segment A component, and $V_B$ and $P_B$ represent the volume fraction and oxygen permeability coefficient, respectively, of the segment B component ($V_A \cdot P_A + V_B \cdot P_B$ will hereinafter be abbreviated as $P_{pm}$). On the other hand, when the two segments are arranged in layers, the resulting shaped article provides a so-called series model. The oxygen permeability P of this shaped article is given by $P = (V_A/P_A + V_B/P_B)^{-1}$. When the microdomains are arranged at random or a random copolymer is used, it is difficult to assume an exact model. However, it is known that, so long as the volume fraction of segment B is in the range of 30 to 70%, the oxygen permeability of the resulting shaped article is at most 0.2–0.4 time that of the parallel model. Accordingly, an described previously, the use of a random copolymer makes it difficult to achieve a good balance between oxygen permeability and mechanical strength.

However, the shaped article of the present invention is characterized by having a high oxygen permeability which is equal to $(0.5 \sim 1) \times P_{pm}$. As is evident from the above discussion, a shaped article having an oxygen permeability within the aforesaid range can be obtained by creating a structure in which segment B extends continuously from one surface thereof to the other. If a shaped article can be made so as to provide a perfect parallel model, its oxygen permeability will be equal to $P_{pm}$. However, some variations are permissible. In practice, a good balance between oxygen permeability and mechanical strength can be achieved if the oxygen permeability of the shaped article is not less than $0.5 \times P_{pm}$. In the above equations, $P_A$ and $P_B$ can be determined by preparing a homopolymer of each segment component and measuring its oxygen permeability coefficient. The volume fractions $V_A$ and $V_B$ are assumed to be given by the following equations:

$$V_A = \frac{\rho_B \cdot W_A}{\rho_B \cdot W_A + \rho_A \cdot W_B}$$

$$V_B = \frac{\rho_A \cdot W_B}{\rho_B \cdot W_A + \rho_A \cdot W_B}$$

where $W_A$ and $W_B$ represent the weight fractions of segments A and B, respectively, $\rho_A$ represents the specific gravity of the homopolymer of the segment A component, and $\rho_B$ represents the specific gravity of the homopolymer of the segment B component.

A shaped article having the above-described structure can be made, for example, by dissolving the above-defined block copolymer in a solvent having a solubility parameter of 7.3 to 9.2 $cal^{\frac{1}{2}} \cdot cm^{-3/2}$, casting the resulting solution, and then removing the solvent therefrom.

The solvent used for this purpose has a solubility parameter of 7.3 to 9.2 $cal^{\frac{1}{2}} \cdot cm^{-3/2}$ and preferably 8.4 to 9.0 $cal^{\frac{1}{2}} \cdot cm^{-3/2}$. This solubility parameter is a value calculated from physical quantities (such as heat of vaporization) and chemical structure. A detailed explanation thereof can be found, for example, in "Polymer Handbook", 2nd Edition, Vol. VI, pp. 337–359, John Wiley & Sons. Specific examples of such solvents include toluene (8.9), carbon tetrachloride (8.6), methyl isobutyl ketone (8.4) and diethyl ketone (8.8), the value given in parentheses after each solvent being its solubility parameter.

If a shaped article is made from a polymer solution prepared with such a solvent, it is possible to create a structure in which the block copolymer has undergone a microscopic phase separation into segments A and B and, moreover, segment B extends continuously from one surface of the shaped article to the other. Furthermore, in the structure having undergone microscopic phase separation, the size of the microdomains formed by the gathering of each type of segments is smaller than the wavelengths of visible light. Thus, the microdomains do not scatter light and, therefore, give a transparent shaped article.

If the solubility parameter of the solvent is less than 7.3 $cal^{\frac{1}{2}} \cdot cm^{-3/2}$, the solution of the block copolymer (a) will not be homogeneous, while if it is greater than 9.2 $cal^{\frac{1}{2}} \cdot cm^{-3/2}$, the resulting shaped article will have unduly low oxygen permeability. Even if a solvent having a solubility parameter of 7.3 to 9.2 $cal^{\frac{1}{2}} \cdot cm^{-3/2}$ is used, the block copolymer (a) may be barely soluble or insoluble, depending on the types of components thereof and the composition thereof. Accordingly, the solvent and the casting conditions should be suitably chosen so as to give a homogeneous solution or a colloidal solution. Although the proper concentration of the block copolymer solution may vary according to the shape of the desired shaped article, it is preferably in the range of about 10 to 200 g/l.

In the practice of the present invention, a desired shaped article can be made by preparing a solution of the above-described block copolymer, spreading it within, or pouring it into, a suitable mold corresponding to the desired shaped article, and then removing the solvent therefrom by evaporation or similar process. Where the solvent is removed by evaporation, it is preferable to evaporate the solvent at a temperature below the boiling point of the solvent and at a rate of not greater than 0.5 ml/cm²·hr. After the shaped article is obtained by evaporation of the solvent, it is preferably post-dried to expel any residual solvent therefrom. For this purpose, it is preferable to vacuum-dry the shaped article while heating it to a temperature below its softening point. If it is desired to make a shaped article of large thickness or to control the thickness of a shaped article, this can be accomplished by forming a plurality of thin shaped articles and bonding them by the application of pressure or with the aid of the aforesaid solvent or solution. Alternatively, this can also be accomplished by spreading the aforesaid solution over, or pouring it onto, a shaped article and removing the solvent therefrom.

The shaped articles made in the above-described manner have a structure in which segment B having high oxygen permeability extends continuously from one surface thereof to the other. Moreover, the size of the microdomains formed by each of segments A and B ranges from several nanometers to several tens of nanometers and is smaller than the wavelengths of visible light. Accordingly, these shaped articles have good transparency and high oxygen permeability.

The molded articles of the present invention can take various forms including films, sheets and lenses. In the case of films, they are useful as oxygen-permeable membranes or highly oxygen-permeable, transparent packaging materials. In the case of membranes, they may be made into various forms including flat membranes, tubular membranes and hollow fiber membranes. Moreover, shaped articles having a lens form of proper thickness are useful as contact lenses and intraocular implants having good transparency and high oxygen permeability. Furthermore, the use of sheet-like shaped articles makes it possible to fabricate transparent and high oxygen-permeable endoscope windows or vessels.

The second aspect of the present invention will be specifically described hereinbelow.

The block copolymer (b) or graft copolymer (c) used in the second aspect of the present invention contains an organopolysiloxane as one component. Although useful organopolysiloxanes include dialkylpolysiloxanes, diphenylpolysiloxane and copolymers thereof, dimethylpolysiloxane is preferably used because of its high oxygen permeability.

The compounds which can be used as the other component constituting the block copolymer (b) or graft copolymer (c) include, for example, polymers derived from monomers having a vinyl group, such as poly(meth)acrylates and polystyrene; polycarbonates such as bisphenol A-derived polycarbonates; and polyesters such as polyarylates and polyethylene terephthalate. Among these compounds, polymers derived from monomers having a vinyl group and polyarylates are preferred, and polymethyl methacrylate is most preferred.

Where the graft copolymer (c) is used in the practice of the present invention, the organopolysiloxane may constitute either the backbone chain or the side chains. A graft copolymer containing an organopolysiloxane as the backbone component can be obtained by polymerizing an organosiloxane and then polymerizing a vinyl monomer as the branch component. A graft copolymer containing an organopolysiloxane as the branch component can be relatively easily obtained by copolymerizing an organopolysiloxane having a methacryloyloxy or vinyl group at one end and a vinyl monomer such as methyl methacrylate. The latter process is especially preferred because it is easy to obtain a polymer containing no insoluble matter. The number average molecular weight of the organopolysiloxane used in the copolymer (b) or (c) is preferably in the range of 700 to 300,000. If the number average molecular weight is less than 700, the resulting shaped article will have insufficient oxygen permeability, while if it is greater than 300,000, the resulting shaped article will tend to show a reduction in transparency.

The content of the organopolysiloxane component in the copolymer (b) or (c) preferably ranges from 15% (inclusive) to 85% (not inclusive), as expressed in terms of volume fraction. If the content is less than 15%, the resulting shaped article will tend to have insufficient oxygen permeability, while if it is 85% or greater, the resulting shaped article will tend to show a reduction in surface hardness and tear strength. The number average molecular weight of the copolymer (b) or (c) is preferably not less than 10,000 and more preferably in the range of 20,000 to 1,000,000. If the number average molecular weight is less than 10,000, it may be difficult to form the copolymer (b) or (c) into fibers. The volume fraction of the organopolysiloxane component can be calculated in the same manner as described above for the volume fraction of each component in the block copolymer (a).

In this aspect of the present invention, the fibers consisting chiefly of the aforesaid copolymer (b) or (c) may be ones formed of the copolymer (b) or (c) alone, or ones formed of a mixture of the copolymer (b) or (c) and at least one other polymer. Where the fibers are formed of such a mixture, it is preferable that the other polymer have good compatibility with the copolymer (b) or (c). It is also preferable that the other polymer comprise a polymer analogous to the non-organopolysiloxane component of the copolymer (b) or (c) or a polymer composed chiefly of an organopolysiloxane. The content of the copolymer (b) or (c) in the mixture is preferably not less than 20%, as expressed in terms of volume fraction. If the content is less than 20%, the resulting shaped article will tend to have unduly low oxygen permeability.

In this aspect of the present invention, a material consisting essentially of a block copolymer (b) or graft copolymer (c) containing, as one component, an organopolysiloxane having high oxygen permeability is spun under stretched conditions, and the resulting fibers are bundled and united to form a shaped article having high oxygen permeability in the direction of the fiber axis. The thickness of the fibers may be within the range of ordinary fiber thicknesses, but is preferably 200 $\mu$m or less. The fibers may be formed of the block copolymer (b) or graft copolymer (c) alone or a homogeneous mixture of such a copolymer and another polymer. Alternatively, they may be sheath-core type composite fibers in which the core consists of the block copolymer (b) or graft copolymer (c) or a material enriched therewith and the sheath consists of another polymer. Alternatively, the fibers may be sea-island type fibers in which the islands consist of the block copolymer (b) or graft copolymer (c) or a material enriched therewith and the sea consists of another polymer.

The shaped articles of the present invention can be made by bundling the fibers formed in the above-described manner and fusing or bonding them together. The size of the fiber bundle may be suitably chosen according to its intended use. In order to fabricate contact lenses or intraocular implants, for example, the fiber bundle preferably has a diameter of about 5 to 15 mm. Where the fibers are united by fusing, it is preferable to fuse them at a temperature in the vicinity of the softening point thereof. Where the fibers are united by bonding, a commercially available adhesive may be used. However, from the viewpoint of transparency and adhesion strength, it is preferable to use, as the adhesive, the organopolysiloxane or other component constituting the fibers. For example, polymethyl methacrylate or a copolymer containing it, or a silicon-containing polymethacrylate or a copolymer containing it, is preferably used as the adhesive.

Although any silicon-containing polymethacrylate can be used, it is preferable to use a compound within the scope of the above general formula (1).

The adhesive can contain, as cross-linkable components, multifunctional methacrylates such as ethylene glycol dimethacrylate and allyl methacrylate.

Where the fiber-forming copolymer (b) or (c) is a copolymer of dimethylpolysiloxane and polymethyl methacrylate, it is preferable to use, as the adhesive, a copolymer composed chiefly of methyl methacrylate and a silicon-containing methacrylate. This adhesive may also be produced by impregnating a fiber bundle with a monomer mixture having the above-described composition and then subjecting the monomer mixture to bulk polymerization. Where a shaped article is made by bonding a fiber bundle with the aid of an adhesive, the volume fraction of the fiber bundle in the molded article is preferably not less than 65%.

In this case, contact lenses and intraocular implants can be made by fusing or bonding a fiber bundle to form a rodlike body, cutting this rodlike body in a direction perpendicular to the fiber axis to obtain shaped articles in button or film form, and then subjecting these shaped articles to fabrication processes such as cutting, pressing, vacuum forming and polishing.

The shaped articles thus obtained are characterized by having higher oxygen permeability in the direction of the thickness (i.e., the direction of the fiber axis). The reason for this is that, in these shaped articles, the block copolymer (b) or graft copolymer (c) has undergone a phase separation into domains consisting of the organopolysiloxane and domains consisting of the other component and, moreover, its spinning has created a structure in which these domains are oriented and interconnected in the direction of the thickness. Accordingly, when shaped articles in film or button form are made in the above-described manner, they have portions in which organopolysiloxane domains extend substantially continuously from one surface to the other and, therefore, exhibit higher oxygen permeability in the direction of the thickness. The size of these microdomains ranges from several nanometers to several tens of nanometers and is smaller than the wavelengths of visible light, thus resulting in transparent shaped articles.

Because of their high oxygen permeability, the above-described shaped articles are suitable for use as materials for the fabrication of contact lenses and intraocular implants. However, membranes, vessels and other products having high oxygen permeability can also be made by forming a rodlike body of larger diameter (for example, by increasing the size of the fiber bundle property or bonding a large number of preformed fiber bundles) and then slicing it.

REFERENCE EXAMPLE 1

Preparation of an A—B type block copolymer (a)

A 500-ml reaction vessel fitted with an argon feed pipe, a stirrer, a thermocouple and a gas outlet pipe was fully purged with argon gas and then charged with 50 ml of tetrahydrofuran, 0.5 ml of tris(dimethylamino)sulfonium bifluoride (as a 0.04M solution in methyl cyanide) and 0.5 ml (2.5 mmoles) of [(2-methoxy-2-methyl-1-propenyl)oxy]trimethylsilane (polymerization initiator). Subsequently, 50 g (0.5 mole) of methyl methacrylate was added dropwise to the stirred reaction system over a period of 10 minutes, during which time care was taken that the temperature thereof did not exceed 50° C. The slow stirring was continued until the temperature of the reaction temperature fell to 30° C. At 30° C., a small amount of sample was taken and subjected to molecular weight measurement by GPC. The resulting polymer was found to have a number average molecular weight of about 20,000, which was substantially the same as the expected value.

Thereafter, 50 g (118.5 mmoles) of tris(trimethylsiloxy)silylpropyl methacrylate was reacted with the above polymer by adding it dropwise to the reaction system over a period of 10 minutes. This resulted in the synthesis of an A—B type block copolymer in which segment A comprised methyl methacrylate and segment B comprised tris(trimethylsiloxy)silylpropyl methacrylate. The resulting polymer was precipitated in water to inactivate the growing ends thereof, and then dried to obtain a white polymer powder. This block copolymer had a number average molecular weight of 40,000.

REFERENCE EXAMPLE 2

Preparation of an A—B—A type block copolymer (a)

Using a reaction vessel similar to that used in Reference Example 1, an A—B type block copolymer was synthesized in the same manner as in Reference Example 1, except that the methyl methacrylate was used in an amount of 25 g (0.25 mole). Thereafter, without inactivating the growing ends of the copolymer, 25 g of methyl methacrylate was reacted therewith by adding it dropwise to the reaction system over a period of 10 minutes. This resulted in the synthesis of an A—B—A type block copolymer. The resulting polymer was precipitated in water to inactivate the growing ends thereof, and then dried to obtain a white polymer powder. This block copolymer had a number average molecular weight of 39,000.

REFERENCE EXAMPLE 3

Preparation of a B—A—B type block copolymer (a)

Using a reaction vessel similar to that used in Reference Example 1, an A—B type block copolymer was synthesized in the same manner as in Reference Example 1, except that the methyl methacrylate was replaced by 25 g (60 mmoles) of tris(trimethylsiloxy)silylpropyl methacrylate and the tris(trimethylsiloxy)silylpropyl methacrylate was replaced by 50 g (0.5 mole) of methylmethacrylate. Thereafter, 25 g (60 mmoles) of tris(trimethylsiloxy)silylpropyl methacrylate was reacted with the above copolymer by adding it dropwise to the reaction system over a period of 10 minutes. This resulted in the synthesis of a B—A—B type block copolymer. The resulting polymer ws precipitated in water to inactivate the growing ends thereof, and then dried to obtain a white polymer powder. This block copolymer had a number average molecular weight of 38,000. All of the polymers obtained in the foregoing reference examples had a $P_{pm}$ of $1.68 \times 10^{-8}$ cm$^3$(STP)·cm/cm$^2$·sec·cmHg.

EXAMPLES 1-5

1.5 g each of the A—B, A—B—A and B—A—B type block copolymers (a) synthesized in the above reference examples were separately dissolved in 30 ml of toluene, carbon tetrachloride or methyl isobutyl ketone. Each of the resulting solutions was spread over the flat bottom surface of a glass dish, allowed to stand at 30° C. for 12 hours so as to evaporate the solvent, and then vacuum-dried at 120° C. for 12 hours to obtain a transparent film having a thickness of about 200 μm. The gas permeabilities of the films thus obtained were measured by means of a gas permeability measuring apparatus (Model GTR-10, manufactured by Yanagimoto Seisakusho) and a gas chromatograph (Model BC-BA, manufactured by Shimadzu Corp.). The oxygen permeability coefficients P (in $cm^3(STP) \cdot cm/cm^2 \cdot sec \cdot cmHg$) so determined are shown in Table 1.

COMPARATIVE EXAMPLES 1-3

Films were formed in the same manner as in Examples 1-4, except that chloroform (with a solubility parameter of 9.3), acetone (9.9) or cyclohexanol (11.4) was used as the casting solvent. The oxygen permeability coefficients of these films were determined and the results thus obtained are also shown in Table 1.

COMPARATIVE EXAMPLE 4

The formation of a film was tried in the same manner as in Example 5, except that n-pentane (with a solubility parameter of 7.0) was used as the casting solvent. However, the resulting solution of the block copolymer was inhomogeneous, so that it was impossible to form a pinhole-free film and determine its oxygen permeability coefficient. Moreover, the resulting film was not transparent.

TABLE 1

| | Block copolymer | Solvent | Solubility parameter | Oxygen permeability coefficient | Light transmittance |
|---|---|---|---|---|---|
| Example 1 | A-B | Toluene | 8.9 | $1.2 \times 10^{-8}$ | 86% |
| Example 2 | A-B | Carbon tetrachloride | 8.6 | $1.1 \times 10^{-8}$ | 87% |
| Example 3 | A-B | MIBK | 8.4 | $8.6 \times 10^{-9}$ | 86% |
| Example 4 | A-B-A | Toluene | 8.9 | $1.0 \times 10^{-8}$ | 86% |
| Example 5 | B-A-B | Toluene | 8.9 | $1.1 \times 10^{-8}$ | 85% |
| Comparative Example 1 | A-B | Chloroform | 8.9 | $4.0 \times 10^{-9}$ | 85% |
| Comparative Example 2 | A-B | Acetone | 8.9 | $2.2 \times 10^{-9}$ | 86% |
| Comparative Example 3 | A-B-A | Cyclohexanol | 11.4 | $2.0 \times 10^{-9}$ | 84% |

Note: The oxygen permeability coefficients are expressed in $cm^3(STP) \cdot cm/cm^2 \cdot sec \cdot cmHG$ (36° C.).

As is evident from Table 1, the films formed according to the process of the present invention were transparent and had high oxygen permeability.

EXAMPLE 6

1.0 g of each of the block copolymers synthesized in Reference Examples 1-3 were separately dissolved in 10 ml of carbon tetrachloride. Each of the resulting solutions was spread within a cylindrical metal vessel having a concave specular surface at the bottom and allowed to stand at 50° C. for 24 hours so as to evaporate the solvent. The resulting shaped article was vacuum-dried at 120° C. for 12 hours to obtain a shaped article having a thickness about 4 mm at the center. This shaped article was immobilized with its concave side down, and its flat side was cut and polished to form a concave surface. Thus, there were obtained a number of lens-shaped articles having a diameter of 10 mm and a thickness of about 100 μm at the center. These lens-shaped articles were transparent and exhibited high oxygen permeability as demonstrated by an oxygen permeability coefficient of about $(1.0 \sim 1.2) \times 10^{-8}$ $cm^3(STP) \cdot cm/cm^2 \cdot sec \cdot cmHg$.

EXAMPLE 7

100 g of dimethylpolysiloxane (with a molecular weight of 3,000) having a methacryloyloxy group at one end and 100 g of methyl methacrylate were dissolved in 400 ml of toluene. After 1.0 g of benzoyl peroxide was added thereto and nitrogen gas was passed therethrough, the solution was reacted at 90° C. for 8 hours. The reacted solution was added dropwise to a solvent mixture composed of methanol and hexane in a ratio of 2:1. Thus, a white graft copolymer (c) was obtained in a 90% yield.

Measurements by GPC revealed that its $M_n$ was 60,000 and its $M_w$ was 120,000.

Using a spinneret having orifices of 0.3 mm diameter, this graft copolymer was spun at a spinning temperature of 230° C., a linear discharge speed of 80 cm/min and a take-up speed of 6,000 cm/min. Thus, there were obtained fibers having a diameter of about 50 μm.

About 60,000 fibers were bundled and packed into an open-ended polytetrafluoroethylene tube having a length of 5 cm and a diameter of 1.5 cm. Then, a monomer mixture composed of methyl methacrylate and tris(trimethylsiloxy)-γ-methacryloyloxypropylsilane in a weight ratio of 6:4 and containing azobisisobutyronitrile in an amount of 0.2% by weight based on the monomers, together with the fiber bundle, was placed in a test tube and deaerated repeatedly to impregnate the fiber bundle with the monomer mixture. Thereafter, the fiber bundle was heated at 80° C. for 12 hours to polymerize the monomer mixture and thereby obtain a shaped article in rod form. This shaped article had a dimethylpolysiloxane content of 35% by weight.

The above-shaped article was sliced in a direction perpendicular to the fiber axis. Both surfaces of this slice were polished to obtain a transparent film having a thickness of 0.5 mm. Its oxygen permeability coefficient in the direction of the thickness (or the direction of the fiber axis) was determined to be $200 \times 10^{-10}$ $cm^3(STP) \cdot cm/cm^2 \cdot sec \cdot cmHg$.

Separately, the above-shaped article was sliced in a direction parallel to the fiber axis. Both surfaces of this slice were polished to obtain a film having a thickness of 0.5 mm. Its oxygen permeability coefficient in a direction perpendicular to the fiber axis was determined to be $10 \times 10^{-10}$ cm$^3$(STP)·cm/cm$^2$·sec·cmHg.

Thus, its oxygen permeability coefficient in the direction of the fiber axis was significantly higher.

EXAMPLE 8

Using the fibers formed in Example 7, a shaped article was made in the same manner as in Example 7, except that methyl methacrylate alone was used in place of the monomer mixture [methyl methacrylate/tris(trimethylsiloxy)-γ-methacryloyloxypropylsilane] with which the fiber bundle had been impregnated. The oxygen permeability coefficient of this shaped article was $180 \times 10^{-10}$ cm$^3$(STP)·cm/cm$^2$·sec·cmHg in the direction of the fiber axis and $0.3 \times 10^{-10}$ cm$^3$(STP)·cm/cm$^2$·sec·cmHg in a direction perpendicular to the fiber axis.

COMPARATIVE EXAMPLE 5

A graft copolymer was prepared in the same manner as in Example 7, except that 70 g of dimethylpolysiloxane (with a molecular weight of 3,000) having a methacryloyloxy group at one end and 130 g of methyl methacrylate were used. This graft copolymer was obtained in a 95% yield. Its $M_n$ was 65,000 and its $M_w$ was 128,000.

This graft copolymer was melted at 240° C. and press-molded to obtain a film having a thickness of 0.5 mm. Its oxygen permeability coefficient was determined to be $80 \times 10^{-10}$ cm$^3$(STP)·cm/cm$^2$ sec·cmHg.

EXAMPLE 9

A reaction vessel fitted with a stirrer was charged with 0.5 kg of a bilaterally diol-terminated dimethylpolysiloxane ($M_n = 3,200$) having the formula given below, 0.16 kg of terephthaloyl chloride and 0.16 kg of isophthaloyl chloride. Then, 6.0 kg of chloroform was added to prepare a homogeneous solution.

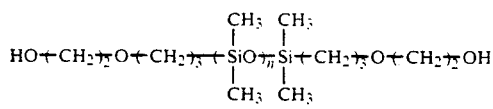

Separately, another homogeneous solution was prepared by adding 0.32 kg of bisphenol A to a mixture of 2.0 kg of chloroform and 0.3 kg of pyridine. This solution was added to the above solution and the resulting mixture was stirred for 8 hours to effect reaction. After completion of the reaction, this mixture was washed with dilute hydrochloric acid and water, and then poured into methanol to obtain 0.95 kg of a poly(arylatedimethylsiloxane) block copolymer (b).

In this block copolymer, the volume fraction of dimethylpolysiloxane was 45%, $M_n$ was 40,000, and $M_w$ was 70,000.

Using this block copolymer, fibers were formed in the same manner as in Example 7, except that the melt spinning temperature was altered to 250° C. These fibers were cut in lengths of 20 mm and placed in a 20 mm×20 mm×40 mm metal mold in such a way that they are oriented in a direction parallel to the bottom surface and juxtaposed with each other. Then, these fibers were pressed at about 190° C. to fuse them together. Thus, there was obtained a 20 mm×20 mm transparent shaped article in which each of the fibers had a substantially regular hexagonal crosssection and no space was left therebetween.

The above-shaped article was cut in a direction perpendicular to the fiber axis to obtain a film having a thickness of 0.5 mm. Its oxygen permeability coefficient was $220 \times 10^{-10}$ cm$^3$(STP)·cm/cm$^2$·sec·cmHg. Separately, the above-shaped article was cut in a direction parallel to the fiber axis to obtain a film. Its oxygen permeability coefficient in a direction perpendicular to the fiber axis was determined to be $60 \times 10^{-10}$ cm$^3$(STP)·cm/cm$^2$·sec·cmHg.

COMPARATIVE EXAMPLE 6

The block copolymer (b) prepared in Example 9 was press-molded at 250° C. to obtain a film having a thickness of 0.5 mm. Its oxygen permeability coefficient was determined to be $90 \times 10^{-10}$ cm$^3$(STP)·cm/cm$^2$·sec·cmHg.

The two types of shaped articles in accordance with the present invention both have a specific higher-order structure. Accordingly, when compared with simple shaped articles consisting of a polymer of the same composition, the shaped articles of the present invention have higher oxygen permeability in a specific direction thereof and, moreover, have such a degree of transparency as to make them suitable for use as lenses. Where these shaped articles are used in applications only requiring an oxygen permeability coefficient equal to those of conventional articles, their tear strength and surface hardness can readily be enhanced by reducing their silicone content accordingly.

We claim:

1. An oxygen-permeable contact lens consisting of a block copolymer (a) of the general formula A—B, A—B—A or B—A—B where 80% by weight or more of the monomer units constituting segment A comprise an alkyl methacrylate having an alkyl group of 1 to 4 carbon atoms, 80% by weight or more of the monomer units constituting segment B comprise monomer units of the general formula $$CH_2=C(CH_3)COOC_mH_{2m}SiX_3 \qquad (1)$$

where m is a whole number of 2 to 5 and each X independently represents a methyl group or

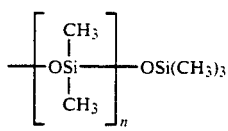

in which n is a whole number of 0 to 30, and the volume fraction of segments B is in the range of 30 to 70%, said shaped article being characterized in that (1) segment A and segment B form microdomains smaller than the wavelengths of visible light, and
(2) the oxygen permeability coefficient thereof is equal to $(0.5 \sim 1) \times (V_A \cdot P_A + V_B \cdot P_B)$ where $V_A$ and $P_A$ represent the volume fraction and oxygen permeability coefficient, respectively, of the segment A component, and $V_B$ and $P_B$ represent the volume fraction and oxygen permeability coefficient, respectively, of the segment B component.

2. A contact lens as claimed in claim 1 wherein the block copolymer (a) has the general formula A—B and the number average molecular weight thereof is in the range of 10,000 to 200,000.

3. A contact lens as claimed in claim 1 wherein the block copolymer (a) has the general formula A—B—A or B—A—B and the number average molecular weight thereof is in the range of 15,000 to 300,000.

4. An oxygen-permeable contact lens obtained by forming fibers consisting chiefly of a block copolymer (b) or graft copolymer (c) containing an organopolysiloxane as one component, fusing or bonding a bundle of said fibers to unite them together, and cutting the resulting body in a direction perpendicular to the fiber axis.

5. A contact lens as claimed in claim 4 wherein the other component of the block copolymer (b) or graft copolymer (c) is a polymer derived from a monomer having a vinyl group, a polycarbonate or a polyester.

6. A contact lens as claimed in claim 4 wherein the organopolysiloxane is dimethylpolysiloxane and the other component of the block copolymer (b) or graft copolymer (c) is methyl methacrylate.

7. A contact lens as claimed in claim 4 which is obtained by forming fibers consisting chiefly of a block copolymer (b) or graft copolymer (c) containing an organopolysiloxane as one component and methyl methacrylate as the other component, and bonding a bundle of said fibers with the aid of a copolymer composed chiefly of methyl methacrylate and a silicon-containing methacrylate 8. A process for the production of transparent contact lenses having high oxygen permeability which comprises the steps of providing a block copolymer of the general formula A—B, A—B—A or B—A—B where segment A comprises an alkyl methacrylate having an alkyl group of 1 to 4 carbon atoms and segment B comprises monomer units of the general formula:

$$CH_2=C(CH_3)COOC_mH_{2m}SiX_3 \quad (1)$$

where m is a whole number of 2 to 5 and each X independently represents a methyl group or

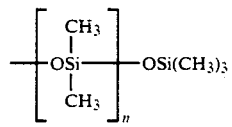

in which n is a whole number of 0 to 30, and the volume fraction of segment B is in the range of 30 to 70%, dissolving the block copolymer in a solvent having a solubility parameter of 7.3 to 9.2 $cal^{\frac{1}{2}} \cdot cm^{-3/2}$, casting the resulting solution, and removing the solvent.

9. A process as claimed in claim 8 wherein the solvent is at least one compound selected from the group consisting of toluene, carbon tetrachloride, methyl isobutyl ketone and diethyl ketone.

* * * * *